United States Patent [19]

Herrmann et al.

[11] Patent Number: 5,965,155
[45] Date of Patent: Oct. 12, 1999

[54] TRANSDERMAL THERAPEUTIC SYSTEM WITH PENTYLENE TETRAZOL AS ACTIVE SUBSTANCE

[75] Inventors: Fritz Herrmann; Thomas Hille, both of Neuwied, Germany

[73] Assignee: LTS Lohmann Therapie-Systeme GmbH & Co., Neuwied, Germany

[21] Appl. No.: 09/093,178

[22] Filed: Jun. 8, 1998

Related U.S. Application Data

[62] Division of application No. 08/392,890, filed as application No. PCT/EP93/02183, Aug. 16, 1993.

[30] Foreign Application Priority Data

Sep. 2, 1992 [DE] Germany .............................. 42 29 230

[51] Int. Cl.⁶ .................................................. A61M 37/00
[52] U.S. Cl. ............................................ 424/449; 514/930
[58] Field of Search ..................... 424/449, 400; 514/929, 930, 811, 823

[56] References Cited

U.S. PATENT DOCUMENTS

| | | | |
|---|---|---|---|
| 4,906,488 | 3/1990 | Pera | 424/486 |
| 5,154,929 | 10/1992 | Shibata et al. | 424/449 |
| 5,186,938 | 2/1993 | Sablotsky et al. | 424/449 |
| 5,273,757 | 12/1993 | Jaeger et al. | 424/449 |
| 5,306,503 | 4/1994 | Müller et al. | 424/449 |
| 5,446,070 | 8/1995 | Mantelle | 424/486 |

FOREIGN PATENT DOCUMENTS

| | | |
|---|---|---|
| 0 271 489 | 6/1988 | European Pat. Off. . |
| 3 315 272 | 3/1986 | Germany . |
| 4 110 027 | 10/1992 | Germany . |

OTHER PUBLICATIONS

Keshary et al., Drug Development and Industrial Pharmacy, vol. 11 pp. 1213–1253 (1985).

Heilmann, Therapeutische Systeme, Konzept und Realisation programmierter Arzneiverabreuichung, 4th Edition 1984 pp. 26–39.

Erickson, Advances in Experimental Medicine and Biology,k vol. 126 Biological Effects of Alcohol (1980) pp. 551–559.

*Primary Examiner*—Edward J. Webmann
*Attorney, Agent, or Firm*—Wenderoth, Lind & Ponack, L.L.P.

[57] ABSTRACT

The invention relates to a pharmaceutic product as well as to a process for its production for a transdermal application in the prophylaxis and treatment of vasodilations, said pharmaceutic product comprising at least one skin-compatible auxiliary agent and portions of an active substance, characterized in that said pharmaceutic product contains as active substance pentetrazole.

14 Claims, No Drawings

TRANSDERMAL THERAPEUTIC SYSTEM WITH PENTYLENE TETRAZOL AS ACTIVE SUBSTANCE

This application is a divisional of application Ser. No. 08/392,890, filed Mar. 1, 1995, file as application No. PCT/EP93/02183, Aug. 6, 1993.

The invention relates to a pharmaceutical product for a transdermal application for the prophylaxis and treatment of vasodilations in the brain or feelings of ill-health caused by paroxysmal dilation of the blood vessels in the brain. Examples for such disorders are migraine and feelings of ill-health caused by excessive alcohol consumption ("hangover").

Migraine and "hangover" have in common that the symptoms are caused by dilation of blood vessels in the brain. While the vasodilation that leads to hangover is due to the dilating action of ethanol, the causes for migraine are still unknown.

Despite the human problems that migraine entails and despite the enormous damage it causes to the economy, innovation in the drug treatment of this disease has been stagnating. Special drugs for the treatment of "hangovers" have been repeatedly described in the patent literature (e.g. EP 0 271 489). However, in most cases, these are relatively arbitrary combinations of low-potency analgesics, vitamins, provitamins, fructose and antihistamines. Low-potency analgesics, generally also called "headache remedies", in both cases do not remove the cause of the indisposition, i.e. vasodilation, but only suppress the symptom, i.e. the headache. In the case of migraine there is a danger that doses will be excessive, which leads to long-term damages caused by this group of drugs.

For the treatment of nausea and vomiting, metoclopramide, bromopride and domperidone are used. What has been said above about the headache symptom also applies to these symptoms.

It is known to treat severe and long-lasting migraine attacks with genuine and hydrogenated ergot alkaloids, especially with ergotamine or dihydroergotamine. Where the treatment is carried out in intervals, the number and severeness of migraine attacks can be reduced.

Non-drug treatment is also possible. Possible measures in this respect are avoiding excessive intake of food and liquid in the evenings, regular sleep and limiting alcohol consumption. The latter prophylaxis variant clearly shows the relation between migraine and alcohol.

For other forms of migraine, active agents of the following substance groups are mainly used:

betablockers (propanolol and metoprolol),
calcium antagonists (e.g. flunarizine),
serotonine antagonists,
platelet aggregation inhibitors,
α-sympatholytics (e.g. clonidine) and
antidepressants (e.g. amitriptyline)
(Ditzel, P., *Deutsche Apothekerzeitung* 14, 690 (1992)).

The variety of the different groups mentioned above already goes to show that there is no single remedy for the prophylactic treatment of all forms of migraine. Moreover, none of the above-listed pharmaceutics is being used for the prophylaxis and treatment of the consequences of excessive alcohol consumption.

Prophylaxis, however, is essential if migraine or "hangover" are to be avoided, as it is known that timely administration of a migraine remedy prevents an attack. However, migraine remedies have so many side effects that hitherto intake "on suspicion" had to be ruled out.

It is thus the object of the invention to provide a pharmaceutical product for a transdermal application for the prophylaxis and treatment of vasodilation which manifests itself in the form of migraine attacks and attacks of "hangover". Moreover, the mode of application is to be one that does not show the above-described disadvantages of the prior art and above all one that delivers low but constant plasma levels.

This object is achieved by a pharmaceutical product according to the present invention.

A method for production is provided by the invention. Further embodiments of the product and the production are also provided by the invention.

Pentetrazole is a central analeptic and, going by its sites of action, it belongs to the so-called brain stem analeptics. The site of application is the substantia reticularis, where the medularry centres for respiration and circulation are also located. Psychostimulating effects are not present. Pentetrazole has no direct peripheral effects. In the case of a severe barbiturate poisoning involving a risk of respiratory paralysis it can be useful to administer the substance as a first-aid measure.

The effect of pentetrazole is exclusively due to the stimulation of central, vegetative regions, in particular of the vasomotory centre (Europäisches Arzneibuch [European Pharmacopeia], vol. III, Commentary, 2nd improved edition 1982 Wissenschaftliche Verlagsgesellschaft mbH Stuttgart Govi-Verlag GmbH Frankfurt).

The active substance pentetrazole is a system of two fused rings. Two components are the completely hydrogenated azepine ring and tetrazole. Pentetrazole is colourless and crystalline, readily soluble in water, ethanol and chloroform, and chemically very stable. Due to the low melting point of 58° C. to 60° C., there is a tendency to form lumps. Since in pentetrazole there is no NH-function, it does not exhibit any acid properties any more. Its basicity is so low that protonation is only successful with strong acids in a water-free medium.

The usability of pentetrazol as above described is surprising since, despite intense research on the pharmacological effects of pentetrazole, a prophylactic effect of pentetrazole in migraine therapy has so far not been described.

In the therapy of alcohol poisoning, this active substance has up to now only been used for treating respiratory paralysis—the cause of death in cases of ethanol intoxication. Where pentetrazole is used for this purpose, however, its small safety margin is stated as being a disadvantage (Erickson, C. K. Adv. Exp. med. Biol. 126, 551 (1980)).

Because of this small safety margin, an application form must be found for pentetrazole, too, that delivers low but constant plasma levels, since medicaments for prophylaxis must be administered over time, i.e. also on suspicion. Common dosages via the oral route do not lead to low constant blood levels. The transdermal route is more suitable; the administration form may be an ointment, cream, lotion or a transdermal therapeutic system (TTS).

The terms "ointments" and "creams" in this connection are understood to mean semi-solid application forms for rubbing into the skin, with "ointment" being the generic term since, according to the definition, ointment consists of an ointment base and medicinal agent, whereas creams are water-in-oil or oil-in-water emulsions. Lotions, by contrast, are shaken mixtures (=suspensions) for rubbing into the skin which mostly have an aqueous base. Auxiliary agents for preparation of ointments, creams and lotions are known to those skilled in the art. Control of the active substance release does not take place, rather the limiting factor is the capacity of the skin to absorb the active agent. This is different with TTS. TTS are application forms to be applied to the skin which have the appearance of a traditional plaster, and which contain active substances that are to be released via the skin. A therapeutic system may contain one or more active agents which are released at a predetermined rate, continuously, over a predetermined period of time, and to a defined application site ("Heilmann, Klaus: Therapeutische Systeme—Konzept und Realisation programmierter Arzneiverabreichung", 4th edition, Ferdinand Enke Verlag Stuttgart, 1984, page 26).

TTS according to the present invention are plasters having an active substance-impermeable backing layer, an active substance reservoir made of a polymer matrix connected to the backing layer, and, where no other control mechanisms are present, a membrane controlling the release of active substance, further a pressure-sensitive adhesive device for fixing the plaster to the skin, and, if required, a protective layer which is removable prior to application.

Examples for suitable plasters are described, for example, in the German Patent DE 33 15 272. Generally, all plaster forms are suitable, as described, for example, in DE-A-41 10 027.1–35.

The form of TTS preferred by this invention is the variant of the matrix system consisting of active substance-impermeable backing layer, active substance-containing self-adhesive reservoir layer and a removable protective layer.

The active substance-impermeable backing layer may consist of flexible or non-flexible material. Substances that may be used for their production are polymer films and metal foils, such as aluminium foil, which may be used singly or coated with a polymer substrate. Also, textile fabrics may be employed if the components of the reservoir cannot penetrate said textile fabrics due to their physical properties. In a preferred embodiment, the backing layer is a composite material consisting of an aluminized film.

The reservoir layer contains the polymer matrix and the active substance, said polymer matrix ensuring the coherence of the system. The polymer matrix consists of a base polymer and, optionally, common additives.

The choice of base polymer is determined by the chemical and physical properties of pentetrazole. Examples for polymers are rubber; rubber-like synthetic homopolymers, copolymers and blockpolymers; poly(meth)acrylic acids and poly(meth)acrylic acid esters and their copolymers; polyurethanes and silicones. Basically all polymers are suitable that can be used for the production of pressure-sensitive adhesives and which are physiologically acceptable. Especially preferred are those consisting of blockcopolymers on the basis of styrene and 1,3-dienes, as well as polyisobutylenes and polymers based on acrylate and/or methacrylate.

Of the blockcopolymers based on styrene and 1,3-dienes, linear styrene-isoprene or styrene-butadiene blockcopolymers are used first of all.

Preferred acrylate-based polymers are self-crosslinking acrylate copolymers of 2-ethylhexyl acrylate, vinyl acetate and acrylic acid with titanium chelate ester; in the case of non-self-crosslinking acrylate polymers titanium chelate ester is not included.

Suitable polymers that can be added to the base polymer comprise polymethacrylates, esters of hydrogenated colophony and polyvinyls.

Preferred methacrylates are copolymers on the basis of dimethylaminoethyl methacrylates and neutral methacrylic acid esters. As esters of hydrogenated colophony, the methyl and glycerin esters thereof are particularly preferred. Preferred polyolefines are polyisobutylenes and polyvinyl alcohols.

Which types of common additives are used depends on the polymer that has been employed: According to their function, they can, for example, be classified as tackifiers, stabilisers, carriers, plasticizers or softeners, and fillers. Physiologically acceptable substances which are suitable for this purpose are known to those skilled in the art.

The selection of plastizers or softeners depends on the polymer. Especially suitable are higher alcohols such as dodecanol, 2-octyldodecanol, undecanol, octanol, esters of carboxylic acid, with the alcohol component possibly being a polyethoxylated alcohol, diesters of dicarboxylic acid, e.g. di-n-butyladipate, as well as triglycerides, especially medium-chain triglycerides or caprylic/capric acids of coconut oil.

Further examples for suitable plasticizers are polyvalent alcohols, e.g. glycerin and propanediol-(1,2), which also may be esterified with polyethylene glycols. Further examples are saturated or unsaturated, cyclic or linear hydrocarbons such as, for instance, 2,6-dioctylcyclohexane.

The reservoir layer has sufficient self-adhesiveness to ensure long-lasting contact to the skin. The pentetrazole concentration depends on the size of the reservoir area. It may be between 0.1 to 50%-wt. of the polymer matrix.

The strippable protective layer, which is in contact with the reservoir layer and is removed prior to application, consists, for example, of the same materials as are used for the production of the backing layer, provided that they are rendered removable, such as by siliconization. Other removable protective layers are, for example, polytetrafluoroethylene, treated paper, cellophane, polyvinyl-chloride and similar materials. If the laminate of the invention, prior to application of the protective layer, is divided into formats (plasters) suitable for therapy, the protective layer formats which must then be applied may exhibit a projecting end which helps to render said protective layer formats more easily removable.

The transdermal therapeutic system according to the invention is produced by homogeneously mixing, in solution, active substance, plasticizer(s) or softener(s), and optionally auxiliary agents together with components of the pressure-sensitive adhesive reservoir layer, spreading the mixture on the active-substance-impermeable backing layer, and thereafter removing the solvent. After this, the adhesive layer is provided with a protective layer.

In principle, the reverse procedure is possible as well, i.e. the adhesive solution is spread onto the protective layer. In this case, too, the solvents are removed and the system is covered with a backing layer. In principle, the reservoir may also be produced from the melt.

There follows a description of how the product is produced:

At room temperature pentetrazole, plasticizers and optionally further auxiliaries are dissolved in a solution of pressure-sensitive adhesive while stirring. After complete dissolution the resultant solution is spread onto a polyester film of 100 $\mu$m thickness that has been rendered removable. By using an appropriate coating knife a weight per unit area of 125 g/m$^2$ is adjusted. After removing the solvents by drying in the drying cabinet for 10 minutes at 80°, the pressure-sensitive adhesive is covered with a polyester film of about 15 μm thickness and, by using an appropriate cutting tool, plasters of 16 cm² are punched out. After peeling off the siliconized polyester film the plasters are stuck onto pieces of mouse skin and the penetration rate is determined in a diffusion cell in accordance with Chien (Kestrary, P. R., Huag, Y. C., Chien, Y. W., *Drug Develp. & Ind. Pharm.* 11, 1213–1254 (1985)). 0.9% Sodium chloride solution is used as an acceptor medium. The following table lists the formulation components and the penetration rates of the pentetrazole TTS.

In the following the formulation components and penetration capacity will be listed in Examples 1 to 10:

1. The following substances are used as base substances for the matrix:

Acid polyacrylate: A self-crosslinking acrylate copolymer of 2-ethylhexylacrylate, vinyl acetate and acrylic acid was used. The acid value is 40.

Basic methacrylate: A copolymer having cationic character based on dimethylaminoethyl-methacrylate and neutral methacrylic acid esters was used. The mean molecular weight is approx. 150000. The KOH value is ca. 180 (162–198).

Neutral methacrylate: A copolymer of neutral, non-ionic nature, based on methacrylic acid methyl ester and methacrylic acid butyl ester. The mean molecular weight is approx. 200000. The acid value is max. 1.0.

2. The following examples show that pentetrazole has a good capacity to penetrate the skin since almost the entire available amount of pentetrazole diffused through the skin. Thus pentetrazole meets the most important requirement for a controlled transdermal application.

We claim:

1. A method for the treatment of vasodilations in the brain or feelings of ill-health caused by paroxysmal dilation of the blood vessels in the brain which comprises transdermally administering to a human in need of such treatment an effective amount of a pharmaceutical composition comprising at least one skin-compatible auxiliary agent and, as the active substance, pentetrazole (6,7,8,9-tetrahydro-5H-tetrazole(1,5-a)azepine).

2. The method according to claim 1, wherein the transdermal administration is effected by applying to the skin of the human a transdermal therapeutic system comprising said pharmaceutical composition.

3. The method according to claim 1, wherein the human is suffering from a migraine.

4. The method according to claim 2, wherein the human is suffering from a migraine.

5. The method according to claim 1, wherein the human is suffering from feelings of ill-health caused by excessive alcohol consumption.

6. The method according to claim 2, wherein the human is suffering from feelings of ill-health caused by excessive alcohol consumption.

7. The method according to claim 1, wherein said pharmaceutical composition is in the form of an ointment.

8. The method according to claim 1, wherein the pharmaceutical composition is in the form of a cream.

9. The method according to claim 1, wherein the pharmaceutical composition is in the form of a lotion.

10. The method according to claim 2, wherein the transdermal therapeutic system is in the form of a plaster.

11. The method according to claim 10, wherein the plaster comprises an impermeable backing layer, an active

| Exple. No. | Pentetrazole | Plasticizer | Pressure Sensitive Adhesive | Auxiliary | mg PTZ/cm² × 8 h | mg PTZ/cm² × 24 h |
|---|---|---|---|---|---|---|
| 1 | 20 mg | 15 mg 2,6 dioctylcyclohexane | 165 mg acid polyacrylate | — | 0.73 | 1.2 |
| 2 | 20 mg | 15 mg 2-octyldodecanol | 165 mg acid polyacrylate | — | 0.71 | 1.19 |
| 3 | 20 mg | 15 mg n-dodecanol | 165 mg acid polyacrylate | — | 0.74 | 1.25 |
| 4 | 20 mg | 15 mg n-dibutyladipate | 165 mg acid polyacrylate | — | 0.66 | 1.25 |
| 5 | 20 mg | 15 mg triglycerides of medium-chain fatty acids | 165 mg acid polyacrylate | — | 0.53 | 0.88 |
| 6 | 20 mg | 15 mg polyethoxylated glycerin with C8/C10 ethoxy groups, whose free hydroxyl groups are partly esterified with caprylic/capric acids | 165 mg acid polyacrylate | — | 0.57 | 1.06 |
| 7 | 20 mg | 10 mg 2,6-dioctyl-cyclohexane | 165 mg acid polyacrylate | — | 0.54 | 0.88 |
| 8 | 20 mg | 10 mg 1-dodecanol | 165 mg acid polyacrylate | — | 0.76 | 1.25 |
| 9 | 20 mg | 15 mg triglycerides of medium-chain fatty acids | 165 mg acid polyacrylate | — | 0.55 | 0.95 |
| 10 | 20 mg | 10 mg polyethoxylated glycerin with C8/C10 ethoxy groups, whose free hydroxyl groups are partly esterified with caprylic/capric acid | 165 mg acid polyacrylate | — | 0.65 | 1.18 | substance, an active substance reservoir, a pressure-sensitive adhesive and, optionally, a removable protective layer, wherein the active substance reservoir is attached to the backing layer;

the active substance reservoir comprises a polymer matrix, and, where no other control mechanism is present, a membrane controlling the release of said active substance; and the pressure-sensitive adhesive secures the plaster to the skin.

12. The method according to claim 1, wherein the pharmaceutical composition contains 0.1 to 50% by weight of said active substance.

13. The method according to claim 12, wherein the pharmaceutical composition contains 3 to 25% by weight of active substance.

14. The method according to claim 13 wherein the pharmaceutical composition comprises 5 to 15% by weight of active substance.

* * * * *